United States Patent [19]

Bell et al.

[11] Patent Number: 5,405,942
[45] Date of Patent: Apr. 11, 1995

[54] PREPRO INSULIN-LIKE GROWTH FACTORS I AND II

[75] Inventors: Graeme I. Bell; Leslie B. Rall, both of San Francisco; James P. Merryweather, Berkeley, all of Calif.

[73] Assignee: Chiron Corporation, Emeryville, Calif.

[21] Appl. No.: 65,673

[22] Filed: Jun. 16, 1987

Related U.S. Application Data

[63] Continuation of Ser. No. 630,557, Jul. 13, 1984, abandoned.

[51] Int. Cl.⁶ .............. C12N 15/17; C12N 15/12; C07H 21/04; C12Q 1/68
[52] U.S. Cl. .............. 536/23.1; 536/24.31; 435/69.1; 435/69.6; 435/172.3; 435/252.31; 435/252.33; 435/254.2; 435/320.1; 435/6
[58] Field of Search .............. 536/27, 28, 23.1; 435/253, 254, 255, 68, 70, 172.3, 320.1, 69.1, 6, 69.6; 935/4, 8, 13, 4, 69, 72, 73, 74

[56] References Cited

U.S. PATENT DOCUMENTS

| | | | |
|---|---|---|---|
| 4,338,397 | 7/1982 | Gilbert et al. | 435/68 |
| 4,394,443 | 7/1983 | Weissman et al. | 435/68 |
| 4,518,690 | 5/1985 | Guntaka | 536/27 |
| 4,728,609 | 3/1988 | Bhatt et al. | 536/27 |

FOREIGN PATENT DOCUMENTS

| | | |
|---|---|---|
| 035384 | 9/1981 | European Pat. Off. . |
| 036259 | 9/1981 | European Pat. Off. . |
| 128042 | 12/1984 | European Pat. Off. . |
| 128733 | 12/1984 | European Pat. Off. . |
| 135094 | 3/1985 | European Pat. Off. . |
| 8600619 | 1/1986 | WIPO ................... 536/27 |

OTHER PUBLICATIONS

Mullenbach et al, Federation Proceeding 42, abstract No. 434 Apr. 25(1983).
Li et al, Proc. Natl. Aca. Sci., USA, 80 2216–2220, (1983).
Woods et al, Proc. Natl. Aca. Sci., USA, 19 5661–5665, (1982).
Rinderknecht et al, J. Biol. Chem., 253 2769–2776 (1978).
Rinderknecht et al, FEBS. LETT. 89, 283–286 (1978).
Woods et al, PNAS USA, vol. 79, (1982), pp. 5661–5665.
Chemical Abstracts 97:104587r (1982).
Chemical Abstracts 98:101617k (1983).
Chemical Abstracts 102:180060a (1985).
Ullrich et al., *The EMBO Journal,* (1984) 3:361–364.
Jansen et al., *Nature,* (1983) 306:609–611.
Rinderknecht and Humbel, *J. Biol. Chem.,* (1978) 253:2769–2776.
Rinderknecht and Humbel, *FEBS Lett.,* (1978) 89:283–286.
Mullenbach et al., (1983) Federation Proceedings (USA) 42, abstract No. 434.
Biotechnology News (1983) 3:1–3.
Peters et al., (1984) J. Cell. Biochem., vol. 0, No. 8, Part A, p. 295, abstract 0818.
Ullrich et al., (1984) EMBO J. 3:361–364.
Bell et al., (1984) Nature 310:775–777.
Riggs et al., (1979) Am J. Human Genet. 31:531–538.

(List continued on next page.)

*Primary Examiner*—Jacqueline Stone
*Attorney, Agent, or Firm*—Morrison & Foerster

[57] ABSTRACT

Polynucleotide sequences which encode for human prepro insulin-like growth factors are provided. Such sequences are obtained from the human genome, typically by screening a cDNA library obtained from human liver cells. The polynucleotide sequences may be used for cloning and expression of insulin-like growth factors in suitable hosts, as well as for the production of DNA and RNA which may be used as hybridization probes.

*E. coli* strains HB101(phigf1) and HB101(phigf2) were deposited at the ATCC on Jun. 8, 1984, and granted accession nos. 39729 and 39730, respectively.

22 Claims, 3 Drawing Sheets

OTHER PUBLICATIONS

Liu et al., (1983) Biological Abstracts, No. 26016659.

Rutter et al., in *Insulin–Like Growth Factors Somatomedins*, pp. 629–640 (E. M. Spencer ed. 1983).

Yang et al., in *Insulin–Like Growth Factors Somatomedins*, pp. 603–610 (E. M. Spencer ed. 1983).

Massague et al., (1982) J. Biol. Chem. 257:5038–5045.

Kurjan et al., (1982) Cell 30:933–943.

Kurjan et al., Abstracts of Papers presented at the 1981 Cold Spring Harbor Meeting on The Molecular Biology of Yeast, p. 242.

Miller et al., (1981) Drug Development Research, vol. 1, pp. 435–454.

Talmadge et al., (1980) Proc. Natl. Acad. Sci. (USA) 77:3988–3992.

Meyhack et al., (1982) Experientia 38:745.

Emr et al., (1980) Proc. Natl. Acad. Sci. 80:7080–7084.

Li et al., (1983) Proc. Natl. Acad. Sci. 80:2216–2220.

Davis et al., (1980) Nature 283:433–438.

Tuite et al., (1982) EMBO. J. 1:603–608.

Hitzeman et al., (1983) Science 219:620–625.

Roggen–Kamp et al., (1981) Proc. Natl. Acad. Sci. 78:4466–4470.

```
        -14                 -10
        Leu Ala Leu Cys Leu Leu Thr Phe Thr Ser Ser Ala Thr Ala
     AC CUG GCG CUG UGC CUG CUC ACC UUC ACC AGC UCU GCC ACG GCU  44
      1                               10
     Gly Pro Glu Thr Leu Cys Gly Ala Glu Leu Val Asp Ala Leu Gln
     GGA CCG GAG ACG CUC UGC GGG GCU GAG CUG GUG GAU GCU CUU CAG  89
                     20                                       30
     Phe Val Cys Gly Asp Arg Gly Phe Tyr Phe Asn Lys Pro Thr Gly
     UUC GUG UGU GGA GAC AGG GGC UUU UAU UUC AAC AAG CCC ACA GGG 134
                                          40
     Tyr Gly Ser Ser Ser Arg Arg Ala Pro Gln Thr Gly Ile Val Asp
     UAU GGC UCC AGC AGU CGG AGG GCG CCU CAG ACA GGU AUC GUG GAU 179
                         50                                   60
     Glu Cys Cys Phe Arg Ser Cys Asp Leu Arg Arg Leu Glu Met Tyr
     GAG UGC UGC UUC CGG AGC UGU GAU CUA AGG AGG CUG GAG AUG UAU 224
                                                  70
     Cys Ala Pro Leu Lys Pro Ala Lys Ser Ala Arg Ser Val Arg Ala
     UGC GCA CCC CUC AAG CCU GCC AAG UCA GCU CGC UCU GUC CGU GCC 269
                         80                                   90
     Gln Arg His Thr Asp Met Pro Lys Thr Gln Lys Glu Val His Leu
     CAG CGC CAC ACC GAC AUG CCC AAG ACC CAG AAG GAA GUA CAU UUG 314
                                         100                 105
     Lys Asn Ala Ser Arg Gly Ser Ala Gly Asn Lys Asn Tyr Arg Met
     AAG AAC GCA AGU AGA GGG AGU GCA GGA AAC AAG AAC UAC AGG AUG 359
     AM
     UAG GAAGACCUCCU GAGGAGUGAAGAGUGACAUGCCACCGCA GGAU CCUUUGCUCUGCA 419
     CGAGUUACCUGUUAAACUUUGGAACACCUACCAAAAAAUAAGUUUGAUAACAUUUAAAAG 479
     AUGGGCGUUUCCCCCAAUGAAAUACACAAGUAAACAUUCCAACAUUGUCUUUAGGAGUGA 539
     UUUGCACCUUGCAAAAAUGGUCCUGGAGUUGGUAGAUUGCUGUUGAUCUUUUAUCAAUAA 599
     UGUUCUAUAAAAAAAAAAAAAA
```

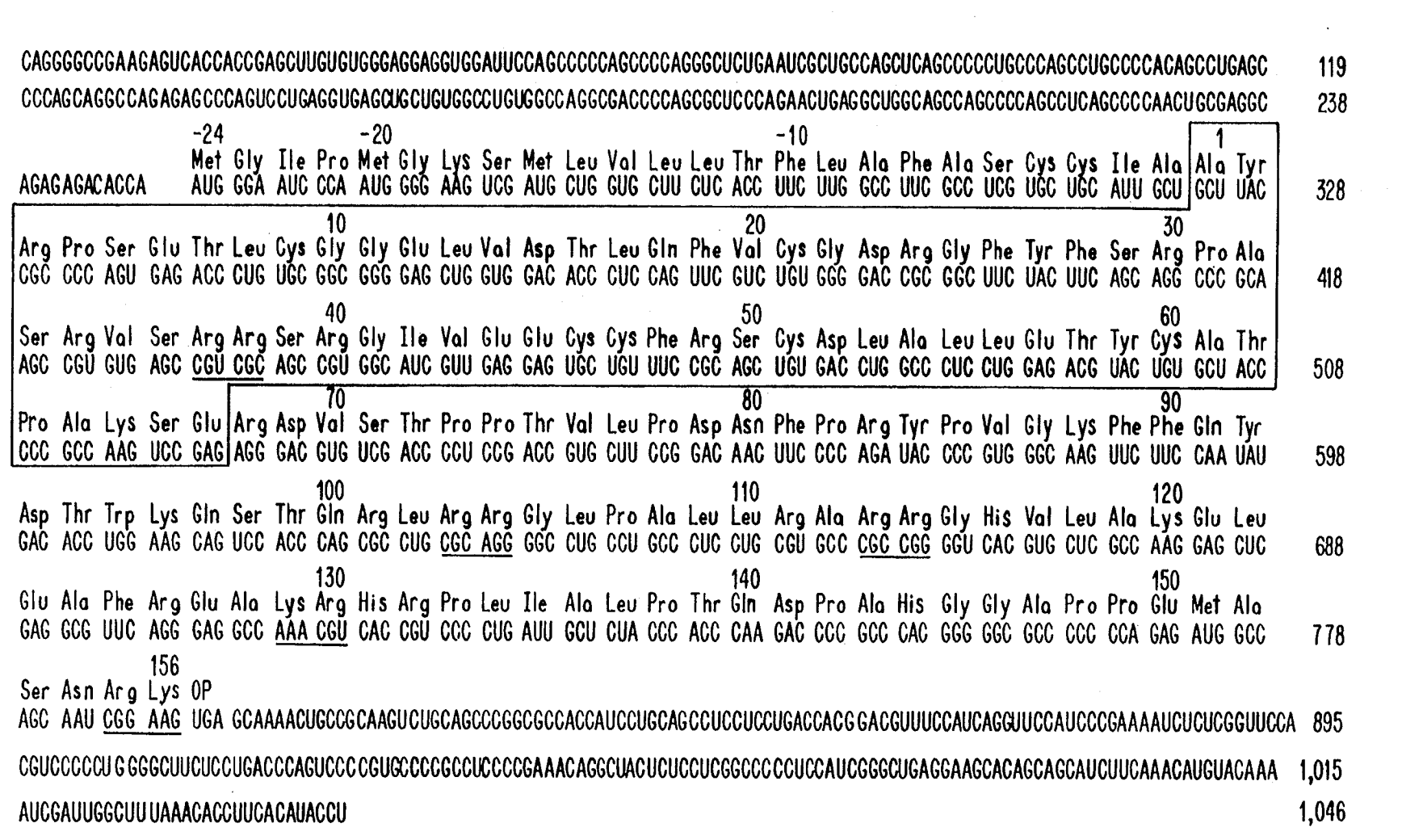

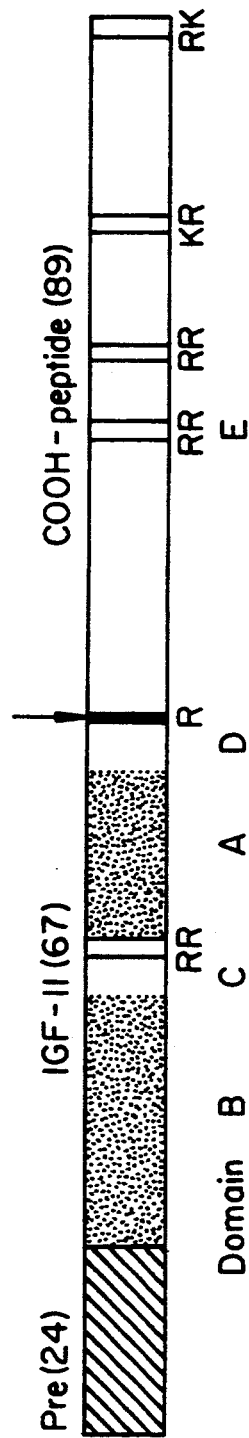
FIG._3.
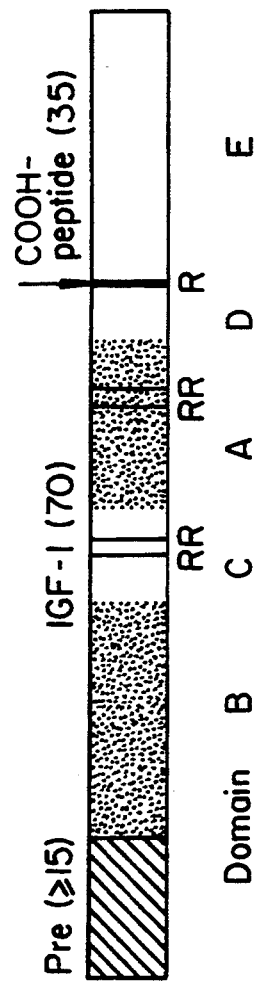
FIG._4.

PREPRO INSULIN-LIKE GROWTH FACTORS I AND II

This application is a continuation of application Ser. No. 630,557, filed 13 Jul. 1984, now abandoned.

BACKGROUND OF THE INVENTION

1. Field of the Invention

It is suspected that somatic growth which follows the administration of growth hormones in vivo is mediated through a family of mitogenic, insulin-like peptides whose serum concentrations are growth hormone dependent. These polypeptides include somatomedin-C, somatomedin-A, and insulin-like growth factors I and II (IGF-I and IGF-II). IGF-I and IGF-II are single chain serum proteins of 70 and 67 amino acids, respectively, and there is evidence that they are identical to somatomedin-C and somatomedin-A. Although IGF-I and IGF-II can be isolated from human serum, such separation at best provides only limited quantities of the growth factors. It would thus be of great scientific and clinical interest to be able to produce relatively large quantities of the growth factors by recombinant DNA techniques. In order to do so, it is necessary to have DNA sequences which encode for IGF-I and IGF-II. In particular, it would be desirable to derive such DNA sequences from their natural source, i.e., human genetic information (RNA or DNA).

2. Description of the Prior Art

The amino acid sequences for human insulin-like growth factors I and II were first determined by Rinderknecht and Humbel (1978) J. Biol. Chem. 253:2769–2776 and Rinderknecht and Humbel (1978) FEBS. Lett. 89:283–286, respectively. The chemical synthesis of biologically active IGF-I has been reported. Li et al. (1983) Proc. Natl. Acad. Sci. USA 80:2216–2220. See also copending application Ser. No. 487,950, filed Apr. 25, 1983, which discloses the expression of synthetic genes for IGF-I and IGF-II in yeast.

SUMMARY OF THE INVENTION

Nucleotide sequences including both DNA and RNA are provided which code for human insulin-like growth factors (IGF) I and II and their corresponding polypeptide precursors. The DNA sequences may be used for production of the IGF and precursor polypeptides and biologically-active portions thereof in microorganisms or cell culture, while both the DNA and RNA sequences are useful as labelled probes in detecting the presence of the growth factor genes and/or mRNA sequences in a natural source. The nucleotide sequences of the present invention are derived from genetic information isolated from human cells, typically liver cells. In the exemplary embodiment, a cDNA library derived from human liver cells is screened with radiolabelled hybridization probes encoding a short nucleotide sequence common to both IGF-I and IGF-II. In this way, DNA sequences encoding for both preproIGF-I and preproIGF-II were detected and isolated.

BRIEF DESCRIPTION OF THE DRAWINGS

FIG. 1 sets forth the nucleotide sequence derived from plasmid phigf1 encoding human preproIGF-I. The predicted amino acid sequence of the prepro protein is provided, and the first amino acid of the mature protein is designated as number 1. The region corresponding to mature IGF-I is boxed, and pairs of basic amino acids are underlined.

FIG. 2 sets forth the nucleotide sequence derived from plasmid phigf2 encoding human preproIGF-II. The predicted amino acid sequence of the prepro protein is numbered with the first amino acid designated as number −24. The region corresponding to mature IGF-II is boxed, and pairs of basic amino acids are underlined.

FIG. 3 is a schematic representation of the structure of preproIGF-II. The proteolytic processing site of proIGF-II is indicated by an arrow; K and R denote lysine and arginine, respectively.

FIG. 4 is a schematic representation of the structure of preproIGF-I. The proteolytic processing site of proIGF-I is indicated by an arrow; K and R denote lysine and arginine, respectively.

DESCRIPTION OF THE SPECIFIC EMBODIMENTS

According to the subject invention, DNA and RNA sequences encoding for human IGF-I and IGF-II prepro polypeptides, or portions thereof, are provided. Such nucleotide sequences are useful for a variety of purposes. Both DNA and RNA sequences including at least 12 bases, more usually at least 18 bases, and frequently having 50 bases or more, can be used as hybridization probes for detecting complementary sequences in genomic DNA or in messenger RNA. Such probes may be used for detecting mutations and/or deletions in humans suspected of suffering from growth deficiencies. Longer DNA sequences may be used for expressing the precursor and/or mature proteins incorporating IGF, or any fragments or analogs thereof. Production of the precursor polypeptides will often be desirable since the precursor will be amenable to post-translational processing in appropriate hosts. The DNA sequences may also be used for the production of mRNA for any of the above purposes.

Both IGF-I and IGF-II are initially translated as "prepro" polypeptides including an amino-termino signal peptide and a carboxy-terminal peptide, referred to as the E domain. The signal peptide directs secretion of the prepro polypeptide across intracellular membranes and is cleaved during such secretion to form the "pro" polypeptide. Mature IGF-I and IGF-II are formed by subsequent proteolysis of the carboxy-terminal E domain from the pro polypeptide.

The nucleotide sequences of the present invention will be derived from human cells, typically by screening a human cDNA or genomic DNA library with hybridization probes capable of detecting a nucleotide sequence predicted from the known amino acid sequences of IGF-I and II. While suitable genomic libraries may be derived from human cells of any origin, it is preferred to utilize cDNA libraries from cells which are known to express the insulin-like growth factors, such as human liver cells and human fetal cells. Suitable hybridization probes may be synthesized by well known techniques and should employ degenerate coding to provide for all possible codons corresponding to each amino acid. In the exemplary embodiment, a human liver cDNA library developed by Woods et al. ((1982) Proc. Natl. Acad. Sci. USA 79:5661–5665) was screened with a 23 base oligonucleotide probe based on an 8 amino acid sequence common to both IGF-I and IGF-II.

The DNA sequences of interest in the present invention may be single or double stranded and will include at least about 12 bases, preferably 18 bases or more, for single stranded oligonucleotides useful as hybridization probes. Double stranded fragments used for expression of polypeptides will usually be longer, typically being at least 18 base pairs corresponding to a sequence of 6 amino acids, more typically being at least the length of the coding region for the mature polypeptide, or a physiologically active fragment thereof. The DNA sequences may extend the entire length of the coding region for the prepro polypeptide, and may include untranslated and/or untranscribed flanking regions on either side of such coding region and/or intervening sequences.

Once the IGF DNA of interest has been isolated from the human cellular source, it will usually be cloned and expanded to provide sufficient amounts of the DNA for the intended use. Once sufficient amounts of the DNA have been obtained, the DNA sequence may be modified in a number of ways. For example, DNA sequences used as hybridization probes will be cleaved to a desired length using restriction enzymes, denatured to single-stranded form, and labelled, typically with a radiolabel, to allow detection. For expression of the mature IGF polypeptides, it may be desirable to excise the coding regions for the mature polypeptide and insert such coding regions into a suitable expression vector. In this way, the mature polypeptide may be expressed in hosts which are incapable of processing the prepro or pro polypeptide. Alternatively, in suitable hosts it may be desirable to employ the coding region for the entire prepro polypeptide either with or without associated flanking or intervening sequences.

The DNA sequences of the present invention may be replicated and expressed in a wide variety of hosts, including prokaryotes, eukaryotes, and mammalian cell culture. The cDNA sequences may be introduced into the host by conventional techniques, usually employing an extrachromosomal element capable of stable replication within the host. Alternatively, the DNA may be introduced directly into the genomic DNA using, e.g., co-transformation as described by Wigler et al. (1979) Cell 16:777-785. Hosts of particular interest include unicellular microorganisms, such as E. coli, S. cerevisiae, and B. subtilis.

A wide variety of suitable extrachromosomal elements exist for the cloning and expression of the IGF DNA sequences of the present invention. The cloning vectors will be selected to include a replication system suitable for the intended host. Suitable expression vectors for mammalian cells are well known in the art and include those having replication systems derived from viral genomes or portions thereof, e.g., SV-40, retroviruses, and the like. Replication systems for E. coli include those derived from various plasmids, such as R6-5, ColE1, RSF, and the like. Particularly convenient is plasmid pBR322 which includes a replication system derived from pMV1. Vectors suitable for yeast include those having a replication system derived from the 2 μm plasmid, autonomously replicating sequences (ars), and the like. Frequently, it will be desirable to have replication systems for both E. coli and a higher organism, e.g., yeast, present on the same extrachromosomal element. Such vectors, referred to as shuttle vectors, allow for cloning and amplification of the IGF gene in bacteria, while expression may be achieved in the higher organism with appropriate RNA or post-translational processing, e.g., cleavage of the pro polypeptide at the appropriate site to yield the mature polypeptide, polyadenylation, splicing, and the like.

In addition to the replication system, suitable extrachromosomal elements will usually include at least one marker for each intended host cell which allows for selection or selective pressure to maintain the extrachromosomal element containing the IGF DNA sequence. Convenient markers include biocidal resistance, e.g., antibiotics, heavy metals and toxins; complementation in an auxotrophic host, and the like.

The following examples are offered by way of illustration and not by way of limitation.

EXPERIMENTAL

Methods

Transformants (approximately 9000) from the adult human liver cDNA library of Woods et al. (1982) Proc. Natl. Acad. Sci. USA 79:5661-5655 were grown in 96-well microtiter dishes. The cDNA library was constructed by inserting ds cDNA prepared from mRNA from adult human liver cells into the PstI restriction site of pKT218. Plasmid pKT218 is a pBR322 derivative described by Talmadge et al. (1980) Proc. Natl. Acad. Sci. USA 77:3369-3373. Colonies of transformed E. coli were transferred to Whatman 541 paper, grown, amplified with chloramphenicol, and lysed as described by Gergen et al. (1979) Nucleic Acids Res. 7:2115-2136. Colonies containing IGF sequences were identified by hybridization with a 256-fold degenerate 23 base oligonucleotide which had been labelled with [$\gamma$-$^{32}$P]-ATP and T4 polynucleotide kinase. The oligonucleotide was synthesized manually (Urdea et al. (1983) Proc. Natl. Acad. Sci. USA 80:7461-7465) and purified by electrophoresis in a 8M urea, 20% polyacrylamide gel. The filters were hybridized in 5XSSC (SSC is 0.15M NaCl, 0.015M sodium citrate), 50 mM sodium phosphate, pH 7.0, 0.2% sodium dodecyl sulfate (SDS), 2X Denhardt's (Denhardt (1966) Biochem. Biophys. Res. Commun. 23:641-646), 200 μg/ml, sonicated and denatured salmon testes DNA, and $10^6$ cpm/ml of 32P-labelled oligonucleotide at 30° C. After 16 hr, the filters were washed in 5XSSC and 0.1% SDS at 42° C. for one hour. Hybridizing colonies were identified by autoradiography. The inserted DNA fragments in the plasmids from the hybridizing colonies were sequenced. The sequence of the fragments carrying IGF-I or IGF-II DNA were determined on both strands and across all restriction sites used to initiate sequence determinations by the procedures of Maxam and Gilbert supra. and Sanger et al. (9180) J. Mol. Biol. 143:161-178.

Results

The nucleotide sequence of the hybridization probe was based on an eight amino acid sequence common to the sequences of IGF-I (amino acids 46-53) and IGF-II (amino acids 45-52), as reported by Rinderknecht and Humbel (1978) J. Biol. Chem. 253:2769-2776 and FEBS Lett. 89:283-286. The sequence was as follows.

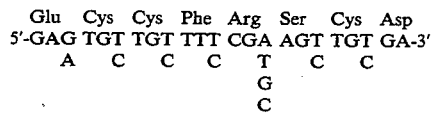

Eight of the approximately 9000 colonies hybridized with this probe, and analyses of the inserted PstI fragments derived from the cloned plasmids revealed that only four of the eight fragments were of different sizes. The nucleotide sequences of each of the four distinct fragments were determined, and the predicted amino acid sequences corresponding to each of the three reading frames compared with the known sequences of IGF-I and IGF-II. The fragments in two of the plasmids (designated phigf 1 and phigf 2) were found to encode IGF-I and IGF-II, respectively. The proteins encoded by the other fragments were not related to IGF.

The plasmid phigf 1 contained a PstI insert of approximately 660 base pairs (bp) which extended from the second nucleotide of the codon for amino acid −15 of the putative signal peptide of the preproIGF-I to the poly A tract and included about 245 bp of 3' untranslated region and a variant polyadenylation signal AATAAT (residues 595–600). The nucleotide sequence and corresponding amino acid sequence are set forth in FIG. 1. The number of the nucleotide at the end of each line is indicated; the region corresponding to mature IGF-I is boxed and pairs of basic amino acids are underlined.

The nucleotide sequence of human preproIGF-II mRNA was deduced from the sequence of the inserted fragment in plasmid phigf 2. Referring to FIG. 2, the predicted amino acid sequence of preproIGF-II is numbered with the first amino acid of preproIGF-II designated as number −24. The region corresponding to mature IGF-II is boxed and pairs of basic amino acids are underlined. An 89 amino acid carboxy-terminal region comprises residues 68–156. The number of the nucleotide at the end of each line is indicated. The B-domain (FIG. 3) of IGF-II comprises residues 1–32, the C-domain comprises residues 33–40, the A-domain comprises residues 41–61, the D-domain comprises residues 62–67, and the carboxyl-terminal E-domain comprises residues 68–156. In comparison, the B-domain of IGF-I (FIG. 4) comprises residues 1–29, the C-domain comprises residues 30–41, the A-domain comprises residues 42–62, the D-domain comprises residues 63–70, and the carboxy-terminal E-domain comprises residues 71–105.

Translation of the IGF-II mRNA from the initial Met (nucleotides 251–253, FIG. 2) predicts an 180 amino acid protein in which the 67 amino acid sequence of IGF-II begins 25 residues from the start. Thus, including the opal termination codon, the coding region is 543 bases. The 5'-untranslated region of the mRNA is at least 250 bases, and the 3'-untranslated region is greater than 253 bases. The cDNA clone phigf 2 lacks a poly A tract and polyadenylation signal.

No other clones encoding preproIGF-II mRNA were revealed when the insert in phigf 2 was used as a probe to rescreen the original 9000 colonies and 6000 additional colonies. A similar experiment using the insert of phigf1 as a probe to screen the same 15,000 colonies revealed, besides phigf1, only a second, identical clone, previously detected in the original screen, and phigf2 which cross-hybridized weakly. Attempts to determine the sizes of human preproIGF-I and preproIGF-II mRNAs by hybridization of the inserts to a northern blot (Thomas (1980) Proc. Natl. Acad. Sci. USA 77:5201–5205) of human adult liver poly A+ RNA were inconclusive, presumably because of the low abundance of these mRNAs (<1/10,000 molecules) in this tissue.

Both IGF-I and IGF-II are secreted proteins, and the 24 residue amino-terminal extension of the latter appears to be the signal peptide. Analysis of the hydrophilicity of preproIGF-II (as described by Hopp and Woods (1981) Proc. Natl. Acad. Sci. USA 78:3824–3828) indicates that the putative signal peptide has a hydrophobic core of 14 residues (amino acids −15 to −2) and a profile similar to other signal peptides. It is concluded that the homologous amino-terminal extension of preproIGF-I also represents a signal peptide of at least 15 amino acids. Interestingly, about 25% of the purified human IGF-II molecules lack Ala 1 (Rinderknecht and Humbel (1978) FEBS Lett. 89:283–286) suggesting that cleavage of the Ala(−1)-Ala(1) peptide bond by the peptidase is preferred but that the Ala(1)-Tyr(2) bond is also cleaved.

The ≧15 and 24 residue amino-terminal extensions are cleaved from preproIGF-I and preproIGF-II, respectively, to produce proIGF-I and proIGF-II. ProIGF-II includes the 89 amino acid carboxyl-terminal extension referred to as the E-domain, and proteolytic processing at Arg 68 is required to produce mature IGF-II. Similarly, proIGF-I contains an E domain but of only 35 amino acids with requisite proteolytic processing to produce mature IGF-I at Arg 71. This carboxyl-terminal extension also has a potential N-linked glycosylation site (residues 92–94:Asn-Ala-Ser), which is absent in the IGF-II precursor. Although proteolytic processing at single basic residues has been reported in the generation of other proteins, including epidermal growth factor (Scott et al. (1982) Science 221:236–240) and growth hormone releasing factor (Gubler et al. (1983) Proc. Natl. Acad. Sci. USA 80:4311–4314; Mayo et al. (1983) Nature 306:86–88), processing occurs more often at pairs of basic amino acids. Only two such sites occur in proIGF-I (indicated by underlining in FIG. 1), both of which are within the mature polypeptide (residues 36–37 and 55–56), and thus remain uncleaved. There are five paired basic amino acids in proIGF-II (underlined in FIG. 2) including one site within mature IGF-II (residues 37–38) that is not cleaved. It is unknown if proteolysis occurs at any of the other pairs of basic residues (proIGF-II) or single basic amino acids within either of the E-domains.

In accordance with the subject invention, polynucleotide sequences are provided which encode insulin-like growth factors I and II. The polynucleotide sequences are derived from human genetic information (either DNA or RNA), typically by screening a cDNA library with an appropriate hybridization probe, and are useful for expression of the prepro polypeptide as well as the mature polypeptide. Additionally, the cloned polynucleotides themselves may be labelled and used as hybridization probes for a variety of purposes, such as genetic screening.

Although the foregoing invention has been described in some detail by way of illustration and example for purposes of clarity of understanding, it will be obvious that certain changes and modifications may be practiced within the scope of the appended claims.

What is claimed is:

1. A composition comprising nucleic acid molecules containing a human sequence encoding insulin-like growth factor (hIGF) substantially free of nucleic acid molecules not containing said hIGF sequence, wherein said hIGF sequence is selected from the group consisting of:

(a) 5'-GGA CCG GAG ACG CUC UGC GGG
    GCU GAG CUG GUG GAU GCU CUU CAG
    UUC GUG UGU GGA GAC AGG GGC UUU

UAU UUC AAC AAG CCC ACA GGG UAU
GGC UCC AGC AGU CGG AGG GCG CCU
CAG ACA GGU AUC GUG GAU GAG UGC
UGC UUC CGG AGC UGU GAU CUA AGG
AGG CUG GAG AUG UAU UGC GCA CCC
CUC AAG CCU GCC AAG UCA GCU-3',
wherein U can also be T;

(b) 5'-GCU UAC CGC CCC AGU GAG ACC CUG
UGC GGC GGG GAG CUG GUG GAC ACC
CUC CAG UUC GUC UGU GGG GAC CGC
GGC UUC UAC UUC AGC AGG CCC GCA
AGC CGU GUG AGC CGU CGC AGC CGU
GGC AUC GUU GAG GAG UGC UGU UUC
CGC AGC UGU GAC CUG GCC CUC CUG
GAG ACG UAC UGU GCU ACC CCC GCC
AAG UCC GAG-3', wherein U can also be T;

(c) nucleic acid sequences complementary to (a) or (b); and (d) fragments of (a), (b) or (c) that are at least 18 bases in length and which will selectively hybridize to human genomic DNA encoding hIGF.

2. A composition according to claim 1 wherein said hIGF is hIGF-I and said hIGF sequence is sequence (a).

3. A composition according to claim 1 wherein said hIGF is hIGF-II and said hIGF sequence is sequence (b).

4. A composition according to claim 2 wherein said nucleic acid molecules comprise the following sequence, wherein U can also be T:

5'-CUG GCG CUG UGC CUG CUC ACC UUC
ACC AGC UCU GCC ACG GCU GGA CCG
GAG ACG CUC UGC GGG GCU GAG CUG
GUG GAU GCU CUU CAG UUC GUG UGU
GGA GAC AGG GGC UUU UAU UUC AAC
AAG CCC ACA GGG UAU GGC UCC AGC
AGU CGG AGG GCG CCU CAG ACA GGU
AUC GUG GAU GAG UGC UGC UUC CGG
AGC UGU GAU CUA AGG AGG CUG GAG
AUG UAU UGC GCA CCC CUC AAG CCU
GCC AAG UCA GCU CGC UCU GUC CGU
GCC CAG CGC CAC ACC GAC AUG CCC
AAG ACC CAG AAG GAA GUA CAU UUG
AAG AAC GCA AGU AGA GGG AGU GCA
GGA AAC AAG AAC UAC AGG AUG-3'.

5. A composition according to claim 3 wherein said nucleic acid molecules comprise the following sequence, wherein U can also be T:

5'-AUG GGA AUC CCA AUG GGG AAG UCG
AUG CUG GUG CUU CUC ACC UUC UUG
GCC UUC GCC UCG UGC UGC AUU GCU
GCU UAC CGC CCC AGU GAG ACC CUG
UGC GGC GGG GAG CUG GUG GAC ACC
CUC CAG UUC GUC UGU GGG GAC CGC
GGC UUC UAC UUC AGC AGG CCC GCA
AGC CGU GUG AGC CGU CGC AGC CGU
GGC AUC GUU GAG GAG UGC UGU UUC
CGC AGC UGU GAC CUG GCC CUC CUG
GAG ACG UAC UGU GCU ACC CCC GCC
AAG UCC GAG AGG GAC GUG UCG ACC
CCU CCG ACC GUG CUU CCG GAC AAC
UUC CCC AGA UAC CCC GUG GGC AAG
UUC UUC CAA UAU GAC ACC UGG AAG
CAG UCC ACC CAG CGC CUG CGC AGG
GGC CUG CCU GCC CUC CUG CGU GCC
CGC CGG GGU CAC GUG CUC GCC AAG
GAG CUC GAA GCG UUC AGG GAG GCC
AAA CGU CAC CGU CCC CUG AUU GCU
CUA CCC ACC CAA GAC CCC GCC CAC

GGG GGC GCC CCC CCA GAG AUG GCC
AGC AAU CGG AAG UGA-3'.

6. A composition according to claim 1 wherein said nucleic acid molecules are DNA.

7. A composition according to claim 1 wherein said nucleic acid molecules are RNA.

8. A composition comprising cellular hosts transformed by a heterologous DNA sequence substantially free of cellular hosts that do not contain said heterologous DNA sequence, wherein said heterologous DNA sequence is a human sequence encoding insulin-like growth factor (hIGF) selected from the group consisting of:

(a) 5'-GGA CCG GAG ACG CTC TGC GGG
GCT GAG CTG GTG GAT GCT CTT CAG
TTC GTG TGT GGA GAC AGG GGC TTT
TAT TTC AAC AAG CCC ACA GGG TAT
GGC TCC AGC AGT CGG AGG GCG CCT
CAG ACA GGT ATC GTG GAT GAG TGC
TGC TTC CGG AGC TGT GAT CTA AGG
AGG CTG GAG ATG TAT TGC GCA CCC
CTC AAG CCT GCC AAG TCA GCT-3';

(b) 5'-GCT TAC CGC CCC AGT GAG ACC CTG
TGC GGC GGG GAG CTG GTG GAC ACC
CTC CAG TTC GTC TGT GGG GAC CGC
GGC TTC TAC TTC AGC AGG CCC GCA
AGC CGT GTG AGC CGT CGC AGC CGT
GGC ATC GTT GAG GAG TGC TGT TTC
CGC AGC TGT GAC CTG GCC CTC CTG
GAG ACG TAC TGT GCT ACC CCC GCC
AAG TCC GAG-3';

(c) nucleic acid sequences complementary to (a) or (b); and (d) fragments of (a), (b) or (c) that are at least 18 bases in length and which will selectively hybridize to human genomic DNA encoding hIGF.

9. A composition according to claim 8 wherein said heterologous DNA sequence is selected from the group consisting of (a), (b) and (c).

10. A composition according to claim 9 wherein said hIGF is hIGF-I and said heterologous DNA sequence is (a).

11. A composition according to claim 9 wherein said hIGF is hIGF-II and said heterologous DNA sequence is (b).

12. A composition according to claim 10 wherein said heterologous DNA sequence comprises the following sequence:

5'-CTG GCG CTG TGC CTG CTC ACC TTC
ACC AGC TCT GCC ACG GCT GGA CCG
GAG ACG CTC TGC GGG GCT GAG CTG
GTG GAT GCT CTT CAG TTC GTG TGT
GGA GAC AGG GGC TTT TAT TTC AAC
AAG CCC ACA GGG TAT GGC TCC AGC
AGT CGG AGG GCG CCT CAG ACA GGT
ATC GTG GAT GAG TGC TGC TTC CGG
AGC TGT GAT CTA AGG AGG CTG GAG
ATG TAT TGC GCA CCC CTC AAG CCT
GCC AAG TCA GCT CGC TCT GTC CGT
GCC CAG CGC CAC ACC GAC ATG CCC
AAG ACC CAG AAG GAA GTA CAT TTG
AAG AAC GCA AGT AGA GGG AGT GCA
GGA AAC AAG AAC TAC AGG ATG-3'.

13. A composition according to claim 11 wherein said heterologous DNA sequence comprises the following sequence:

5'-ATG GGA ATC CCA ATG GGG AAG TCG
ATG CTG GTG CTT CTC ACC TTC TTG

GCC TTC GCC TCG TGC TGC ATT GCT
GCT TAC CGC CCC AGT GAG ACC CTG
TGC GGC GGG GAG CTG GTG GAC ACC
CTC CAG TTC GTC TGT GGG GAC CGC
GGC TTC TAC TTC AGC AGG CCC GCA
AGC CGT GTG AGC CGT CGC AGC CGT
GGC ATC GTT GAG GAG TGC TGT TTC
CGC AGC TGT GAC